(12) United States Patent
Wagstaff

(10) Patent No.: US 10,045,872 B2
(45) Date of Patent: Aug. 14, 2018

(54) REINFORCED JOINT SUPPORT STRAP AND METHOD OF APPLICATION

(71) Applicant: Michael Wagstaff, Farmington, UT (US)

(72) Inventor: Michael Wagstaff, Farmington, UT (US)

( * ) Notice: Subject to any disclaimer, the term of this patent is extended or adjusted under 35 U.S.C. 154(b) by 274 days.

(21) Appl. No.: 15/016,196

(22) Filed: Feb. 4, 2016

(65) Prior Publication Data

US 2017/0224518 A1    Aug. 10, 2017

(51) Int. Cl.
*A61F 5/01* (2006.01)

(52) U.S. Cl.
CPC ............ *A61F 5/0111* (2013.01); *A61F 5/0118* (2013.01)

(58) Field of Classification Search
CPC ........ A61F 5/0111; A61F 5/0118; A61F 5/01; A61F 5/0102; A61F 5/0104
See application file for complete search history.

(56) References Cited

U.S. PATENT DOCUMENTS

| | | | | |
|---|---|---|---|---|
| 4,584,993 A * | 4/1986 | Nelson | ........... | A61F 5/0118 602/21 |
| 4,590,932 A * | 5/1986 | Wilkerson | ........... | A61F 5/0111 602/65 |
| 8,574,180 B2 * | 11/2013 | Tabron | ........... | A61F 5/01 601/148 |
| 9,655,759 B2 * | 5/2017 | Draper | ........... | A61F 5/0111 |
| 2007/0167896 A1 * | 7/2007 | Cooper | ........... | A61F 5/0111 602/27 |
| 2008/0228120 A1 * | 9/2008 | Gill | ........... | A61F 5/0118 602/22 |
| 2009/0247923 A1 * | 10/2009 | Lundberg | ........... | A61F 5/0111 602/27 |
| 2011/0034846 A1 * | 2/2011 | Draper | ........... | A61F 5/0111 602/27 |
| 2012/0078152 A1 * | 3/2012 | Robertson | ........... | A61F 5/0111 602/27 |
| 2015/0238344 A1 * | 8/2015 | Nylund | ........... | A01L 3/00 602/12 |

* cited by examiner

*Primary Examiner* — Kristen Matter
(74) *Attorney, Agent, or Firm* — Steven Rinehart

(57) ABSTRACT

A reinforced support strap and method of application on a joint provides lateral and medial support to a joint and limbs. The support strap comprises, in some embodiments, a resilient body portion having a generally elongated V-shape that encapsulates the joint and is manipulated through rotation or axial movement along the joint and limbs for an enhanced fit. The body portion comprises a base end, an open end, and a pair of termini. The body portion further includes a mount surface that overlays the joint, and an exterior surface. The mount surface adheres to the joint through the use of a fastening mechanism. A reinforcement member, having less resilience than the body portion, may integrates into the body portion through stitching, to provide enhanced stability.

18 Claims, 16 Drawing Sheets

REINFORCED JOINT SUPPORT STRAP AND METHOD OF APPLICATION

FIELD OF THE INVENTION

This invention relates to a reinforced support strap and method of application on a joint, and more particularly relates to a reinforced support strap that stabilizes a joint and limbs.

BACKGROUND

Description of the Related Art

Typically, the prevention of injury to wrists and ankles, as well as the treatment of injured wrists and ankles, requires the provision of pressure and support to the area around the injured ankle. There are many known devices that for this purpose.

It is known that a wrist or ankle strap or orthosis is an externally applied device that is designed and fitted to the body to help control biomechanical alignment, correct or accommodate deformity, and protect and support an injury.

Often, these types of straps/braces can be resilient and worn around the ankle or wrist to protect it or for immobilization while allowing it to heal. Ankle straps are used to immobilize the joint while providing heat and compression to the bones. They are common in injury rehabilitation processes that affect the ankle, being made of rigid fabric such nylon and neoprene that allow limited mobility of the foot and conform to the ankle by a hook and loop fastener. In severe cases, they incorporate metallic plates to better immobilize the joint.

In rehabilitation the ankle and wrist straps/braces are often used to immobilize the ankle in a neutral position, which theoretically minimizes stress at the repair site. These ankle and wrist straps/braces are often used in sports where the ankle is under stress, as in soccer, rugby, or basketball. In many instances, the resilient nature of the strap is insufficient rigidity to ensure sufficient stability to the ankle or wrist. Also, the fastening mechanism on these joint stabilizing mechanism is not strong or consistent enough to retain the strap/brace in the desired location along the wrist or ankle Other proposals have involved stabilizing braces, straps, and orthopedic joint support mechanisms. The problem with these stabilizers is that they do not ensure sufficient stability to the ankle or wrist. Also, the fastening mechanism on these joint stabilizing mechanism is not strong enough to retain the strap/brace in the desired location along the wrist or ankle Even though the above cited joint stabilizing mechanisms meet some of the needs of the market, a reinforced support strap and method of application on a joint, such as an ankle, wrist, or knee is still desired.

SUMMARY

From the foregoing discussion, it should be apparent that a need exists for a reinforced support strap and method of application on a joint. The support strap is configured to provide pressure and lateral and medial support to a joint, such as the wrist or ankle that is susceptible to stress and excessive stretching. In one embodiment, the support strap comprises a resilient body portion having a generally elongated V-shape. The body portion forms a substantial portion of the support strap that encapsulates the joint. The body portion may be manipulated through rotation or axial movement along the limbs for an enhanced fit.

The body portion comprises a base end and an open end. The V-shape of the body portion generally ends at a pair of termini towards the open end. The body portion wraps around the joint to form a snug, compact encapsulation of the joint.

The body portion comprises elasticized members that enable formation of a generally resilient body portion that snugly encapsulates the joint. This immobilizes the joint against lateral and medial movement and provides limited resistance against torsion while allowing forward and backward rotation about the joint. In one embodiment, the body portion wraps around the joint until the termini meet to fasten together.

The body portion further includes a mount surface and an exterior surface. The mount surface overlays the joint during use. In one embodiment, the mount surface adheres to the joint through the use of a fastening mechanism. A removable panel overlays the mount surface. The removable panel may peel off the mount surface to expose the fastening mechanism.

The fastening mechanism may include, without limitation, a hook and loop fastener, an adhesive, and a hook. In one embodiment, the terminus of the body portion is folded back upon itself after wrapping around the joint, so as to join the fastening mechanism to the exterior surface of the body portion. In another embodiment, the fastening mechanism fastens directly on the joint.

The support strap may further include at least one lateral extension that forms at the termini of the body portion. The lateral extension enables attachment to the joint and maintains the snug encapsulation of the body portion around the joint. The lateral extension is configured to stretch in multiple directions to enhance the fit of the body portion. In one embodiment, the at least one lateral extension comprise a pair of spaced-apart parallel lateral extensions. In some embodiment, the lateral may have a secondary removable panel to expose a secondary fastening mechanism.

The support strap may further include at least one medial extension that forms at the base end of the body portion. Similar to the lateral extension, the medial extension enables attachment to the joint and maintains the snug encapsulation of the body portion around the joint. The medial extension is configured to stretch in multiple directions to enhance the fit of the body portion. In one embodiment, the at least one medial extension comprises a pair of medial extensions that extend from the sides of the base end of the body portion. In some embodiment, the medial extension may have a tertiary removable panel to expose a tertiary fastening mechanism.

In one embodiment, the body portion, the at least one lateral extension, and the at least one medial extension are configured to cooperate for immobilizing a joint against lateral and medial mobility, while providing resistance to twisting of a first limb relative to a second limb.

In some embodiments, at least one reinforcement member integrates into the body portion. In one embodiment, the reinforcement member has a generally X shape. The reinforcement member is less resilient than the body portion. Because of the less resilient nature of the reinforcement member, extra support to the joint is consequently provided. Further, when positioned centrally on the body portion, the reinforcement member inhibits undesirable flexing of the joint. In one embodiment, the reinforcement member is a ribbon having a generally X-shape that is stitched along the length of the body portion. In another embodiment, the body portion may be manipulated around the joint to align the reinforcement member with a desired region of the joint.

Another support strap for providing lateral and medial support to a joint is provided, the strap comprising: a body portion, the body portion defined by a generally elongated V-shape, the body portion further defined by a pair of termini, a base end, an open end, an exterior surface, and a mount surface, the body portion comprising an elasticized member configured to enable resilience; a fastening mechanism, the fastening mechanism configured to enable detachable mounting of the strap; a removable panel, the removable panel configured to detachably overlay the fastening mechanism to enable selective operation of the fastening mechanism; at least one lateral extension, the at least one lateral extension configured to extend from the pair of termini of the body portion; at least one medial extension, the at least one medial extension configured to extend from the base end of the body portion, whereby the body portion, the at least one lateral extension, and the at least one medial extension are configured to enable cooperation to immobilize a joint against lateral and medial mobility, while providing resistance to twisting of a first limb relative to a second limb; a pair of Y-shaped reinforcement members, the pair of Y-shaped reinforcement members defined by a lesser resilience than the body portion, the pair of Y-shaped reinforcement members configured to integrate into the body portion and comprising between two and eight fingers; and a connector, the connector configured to join the pair of X-shaped reinforcement members, whereby the at least one reinforcement member is further configured to enhance immobilization of the joint against lateral and medial mobility.

Reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussion of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize that the invention may be practiced without one or more of the specific features or advantages of a particular embodiment. In other instances, additional features and advantages may be recognized in certain embodiments that may not be present in all embodiments of the invention.

These features and advantages of the present invention will become more fully apparent from the following description and appended claims, or may be learned by the practice of the invention as set forth hereinafter.

BRIEF DESCRIPTION OF THE DRAWINGS

In order that the advantages of the invention will be readily understood, a more particular description of the invention briefly described above will be rendered by reference to specific embodiments that are illustrated in the appended drawings. Understanding that these drawings depict only typical embodiments of the invention and are not therefore to be considered to be limiting of its scope, the invention will be described and explained with additional specificity and detail through the use of the accompanying drawings, in which.

DETAILED DESCRIPTION

Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

Furthermore, the described features, structures, or characteristics of the invention may be combined in any suitable manner in one or more embodiments. In the following description, numerous specific details are provided, such as examples of programming, software modules, user selections, network transactions, database queries, database structures, hardware modules, hardware circuits, hardware chips, etc., to provide a thorough understanding of embodiments of the invention. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

It is the object of the present invention to provide a reinforced support strap and method of application on a joint, and more particularly a reinforced support strap that stabilizes a joint and limbs, comprising a resilient body portion having a generally elongated V-shape, a pair of lateral and medial extensions, a mount surface; and further including at least one reinforcement member having less resilience than the body portion, that integrates into the body portion; whereby the body portion and the extensions adheres to the joint through a fastening mechanism; and whereby the reinforcement member is less resilient than the body portion, so as to provide extra support and inhibit flexing of the joint and limbs.

Figure 1:
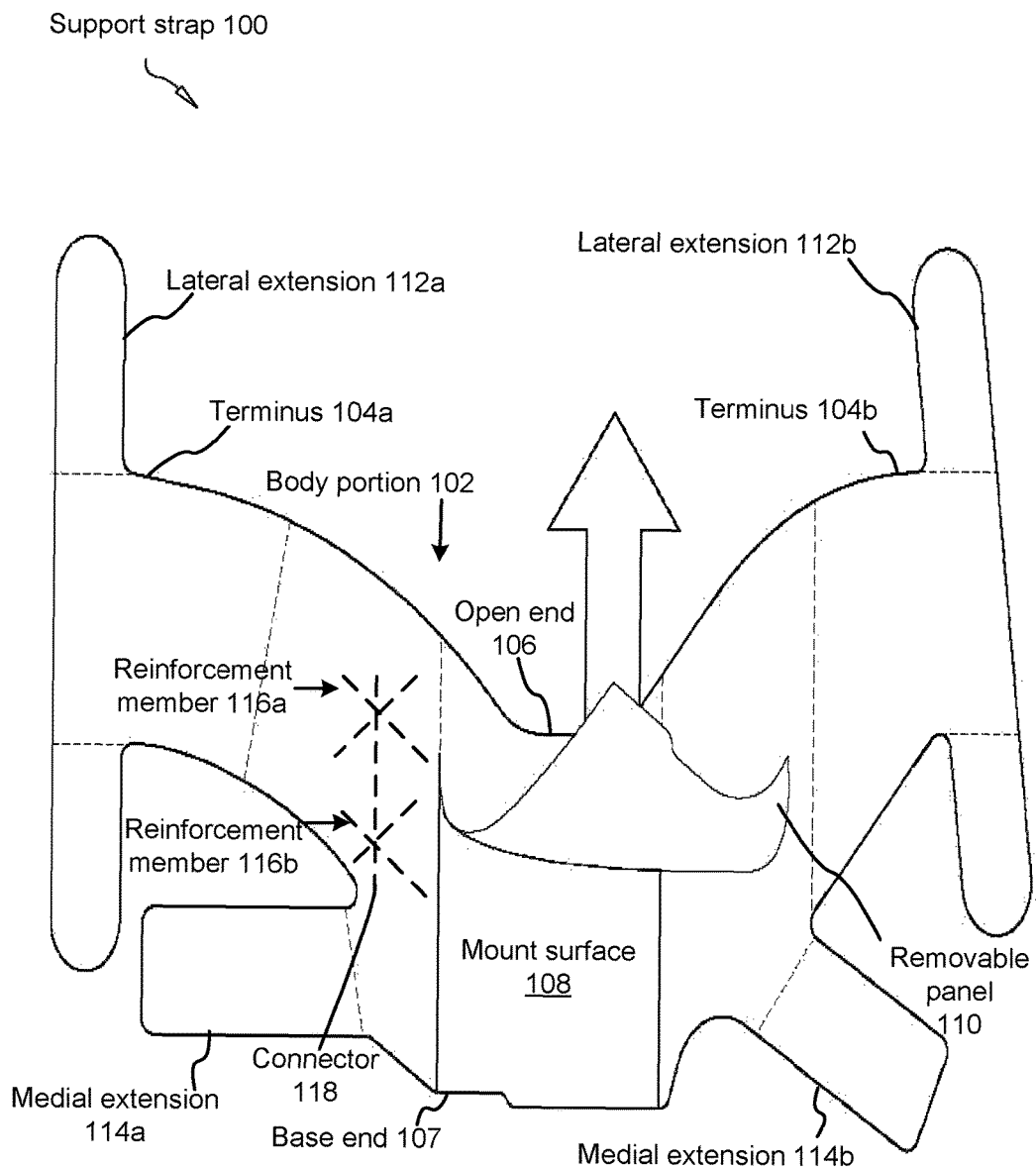
FIG. 1 is a top view illustrating one embodiment of a reinforced joint support strap, in accordance with the present invention.

FIG. 1 depicts a reinforced support strap 100 and method 900 of application on a joint. The support strap 100 is configured to provide pressure and lateral and medial support to a joint 200, such as the wrist or ankle, which is susceptible to stress and excessive stretching. In one embodiment, the support strap 100 immobilizes the joint 200 against lateral and medial mobility, while providing resistance to twisting of a first limb 202 relative to a second limb 204.

Figure 2:
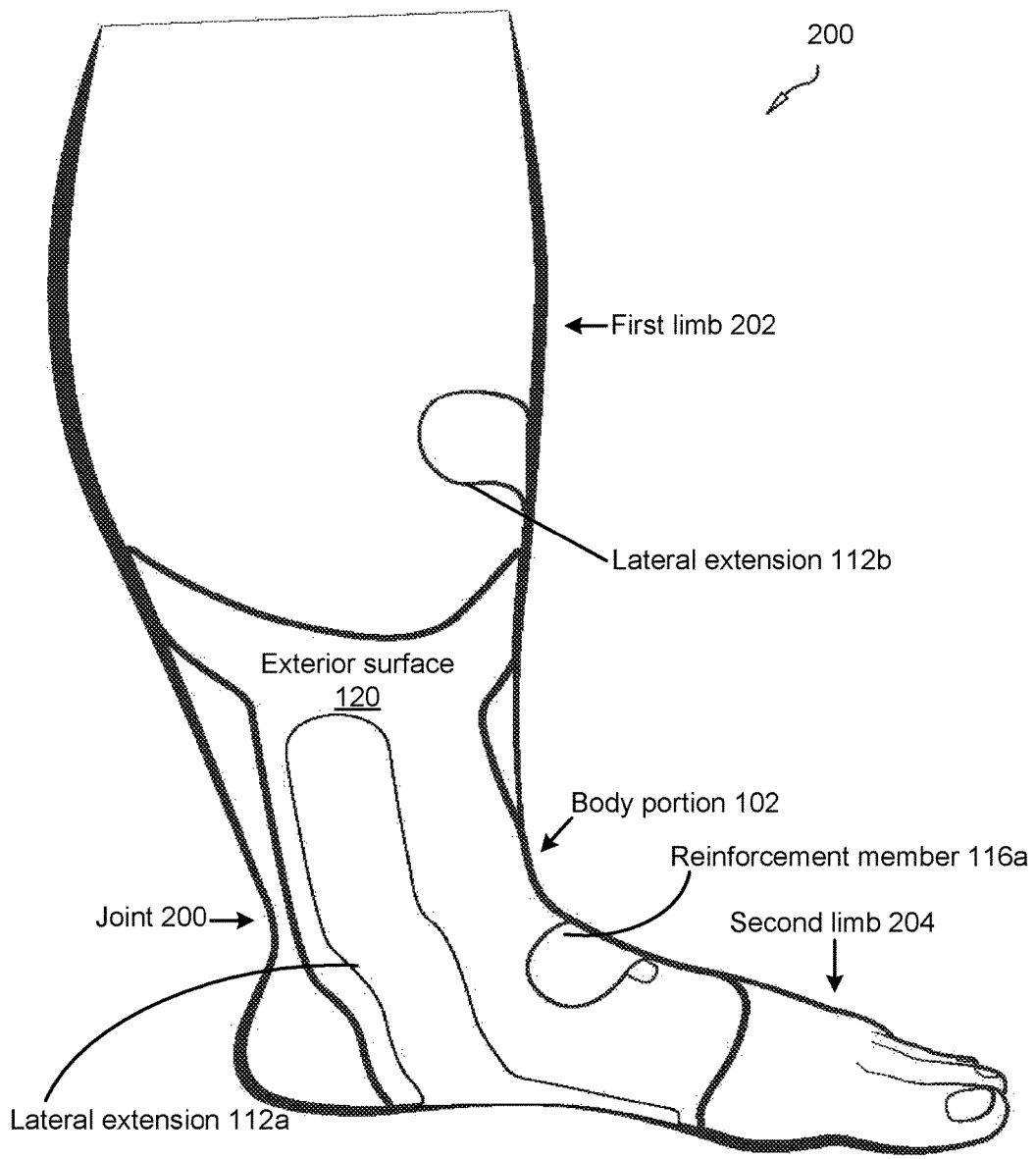
FIG. 2 is an environmental left side perspective view of the reinforced joint support strap of FIG. 1 wrapped around a joint, a first limb, and a second limb, in accordance with the present invention.

For purposes of the present invention, the joint 200 may include an ankle, a wrist, a knee, a hip, and a neck. The first limb 202 may include the calf area of a leg, or a forearm. The second limb 204 may include a foot or a hand. Those skilled in the art will recognize that stabilizing the joint 200 after injury or operation is imperative for proper healing thereof. For example, FIG. 2 illustrates the support strap 100 encapsulating an ankle and portions of an upper region and lower region of the foot. In one alternative embodiment, the support strap 100 is configured to contract a muscle, such as a bicep or calf by wrapping around and applying pressure to the muscle.

In one embodiment, the support strap 100 comprises a resilient body portion 102 having a generally elongated V-shape. The body portion 102 forms a substantial portion of the support strap 100 that encapsulates the joint 200. The body portion 102 may be manipulated through rotation or axial movement along the limbs 202, 204 for an enhanced fit.

In some embodiments, the body portion 102 includes a base end 107 and an open end 106. The V-shape of the body portion 102 generally ends at a pair of termini 104a, 104b towards the open end 106. The body portion 102 forms a substantial portion of the support strap 100 that wraps around the joint 200, the first limb 202, and the second limb 204 to form a snug, compact encapsulation for enhanced stabilization and inhibition of flexing by the joint 200.

The body portion 102 is fabricated from an elongated woven material having elasticized members. Suitable elasticized members may include, without limitation, elastic, rubber, nylon, polyester, and a resilient polymer. The elasticized member enables the body portion 102 to have a generally resilient nature to enable a snug encapsulation of the joint 200 and the limbs. This immobilizes the joint 200 against lateral and medial movement and provides limited resistance against torsion while allowing forward and backward rotation about the joint 200. In one embodiment, the body portion 102 wraps around the joint 200 in a helical motion until the termini 104a, 104b of the body portion 102 meet.

The body portion 102 includes a mount surface 108 and an exterior surface 120. The mount surface 108 engages the joint 200. In one embodiment, the mount surface 108 adheres to the joint 200 through the use of a fastening mechanism. In one alternative embodiment, the mount surface 108 comprises an anti-bacterial composition. In another alternative embodiment, the exterior surface 120 is configured to restrict passage of moisture.

As illustrated in FIG. 1, a removable panel 110 overlays the mount surface 108. The removable panel 110 may peel off the mount surface 108 to expose the fastening mechanism. The fastening mechanism may include, without limitation, a hook and loop fastener, an adhesive, and a hook. In one embodiment, the terminus of the body portion 102 is folded back upon itself after wrapping around the joint 200, so as to join the fastening mechanism to the exterior surface 120 of the body portion 102. In another embodiment, the fastening mechanism fastens directly on the joint 200.

Looking again at FIG. 1, at least one reinforcement member 116a, 116b integrates into the body portion 102. The reinforcement member 116a, 116b is generally less resilient than the body portion 102. Because of the less resilient nature of the reinforcement member 116a, 116b, extra support to the joint 200 is consequently provided. Further, when positioned centrally on the body portion 102, the reinforcement member 116a, 116b inhibits undesirable flexing of the joint 200. In one embodiment, the reinforcement member 116a, 116b is stitched into the body portion 102.

In some embodiments, a connector 118, such as a linear material having less resilience than the body portion 102, may be used to connect two or more resilient members 116a, 116b. The connector 118 may be sued to align the affected area of the joint 200 with the resilient members 116a, 116b to provide greater support to the joint 200 and the limbs.

The support strap 100 may further include at least one lateral extension 112a, 112b that forms at the termini 104a, 104b of the body portion 102. The lateral extension 112a, 112b enables attachment to the joint 200 and maintains the snug encapsulation of the body portion 102 around the joint 200. The lateral extension 112a, 112b is configured to stretch in multiple directions to enhance the fit of the body portion 102. In one embodiment, the at least one lateral extension 112a, 112b comprise a pair of spaced-apart parallel lateral extension 112a, 112bs. In some embodiment, the lateral may have a secondary removable panel 110 to expose a secondary fastening mechanism.

The support strap 100 may further include at least one medial extension 114a, 114b that forms at the base end 107 of the body portion 102. Similar to the lateral extension 112a, 112b, the medial extension 114a, 114b enables attachment to the joint 200 and maintains the snug encapsulation of the body portion 102 around the joint 200. The medial extension 114a, 114b is configured to stretch in multiple directions to enhance the fit of the body portion 102. In one embodiment, the at least one medial extension 114a, 114b comprises a pair of medial extension 114a, 114bs that extend from the sides of the base end 107 of the body portion 102.

Figure 8:
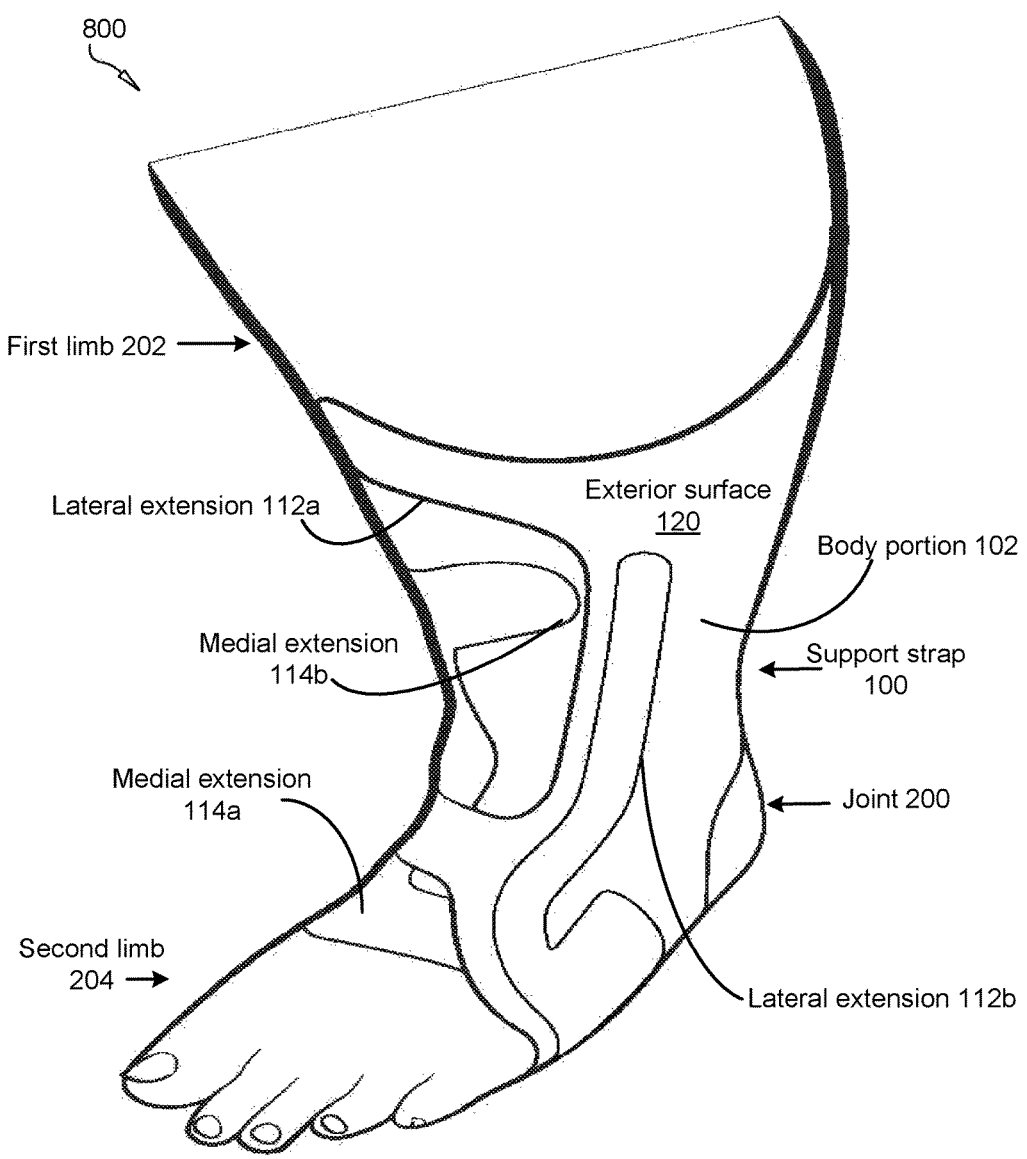
FIG. 8 is an environmental right side perspective view of a joint, a first limb, and a second limb stabilized by the reinforced joint support strap in accordance with the present invention.

In one alternative embodiment, the medial extension 114a, 114b may have a tertiary removable panel to expose a tertiary fastening mechanism. As FIGS. 2 and 8 illustrate, the extensions 112a, 112b, 114a, 114b may be manipulated in multiple directions around the limbs 202, 204, and fastened thereto to achieve a desired fit for the body portion 102.

In some embodiments, any one of the body portion 102, the at least one lateral extension 112a, 112b, and the at least one medial extension 114a, 114b are configured to cooperate for immobilizing a joint 200 against lateral and medial mobility, while providing resistance to twisting of a first limb 202 relative to a second limb 204. In one exemplary use, the body portion 102 supports the base of the feet and the ankle, while the medial extension 114a, 114bs support the upper region of the foot, and the lateral region reinforces the ankle in conjunction with the body portion 102.

Figure 3:
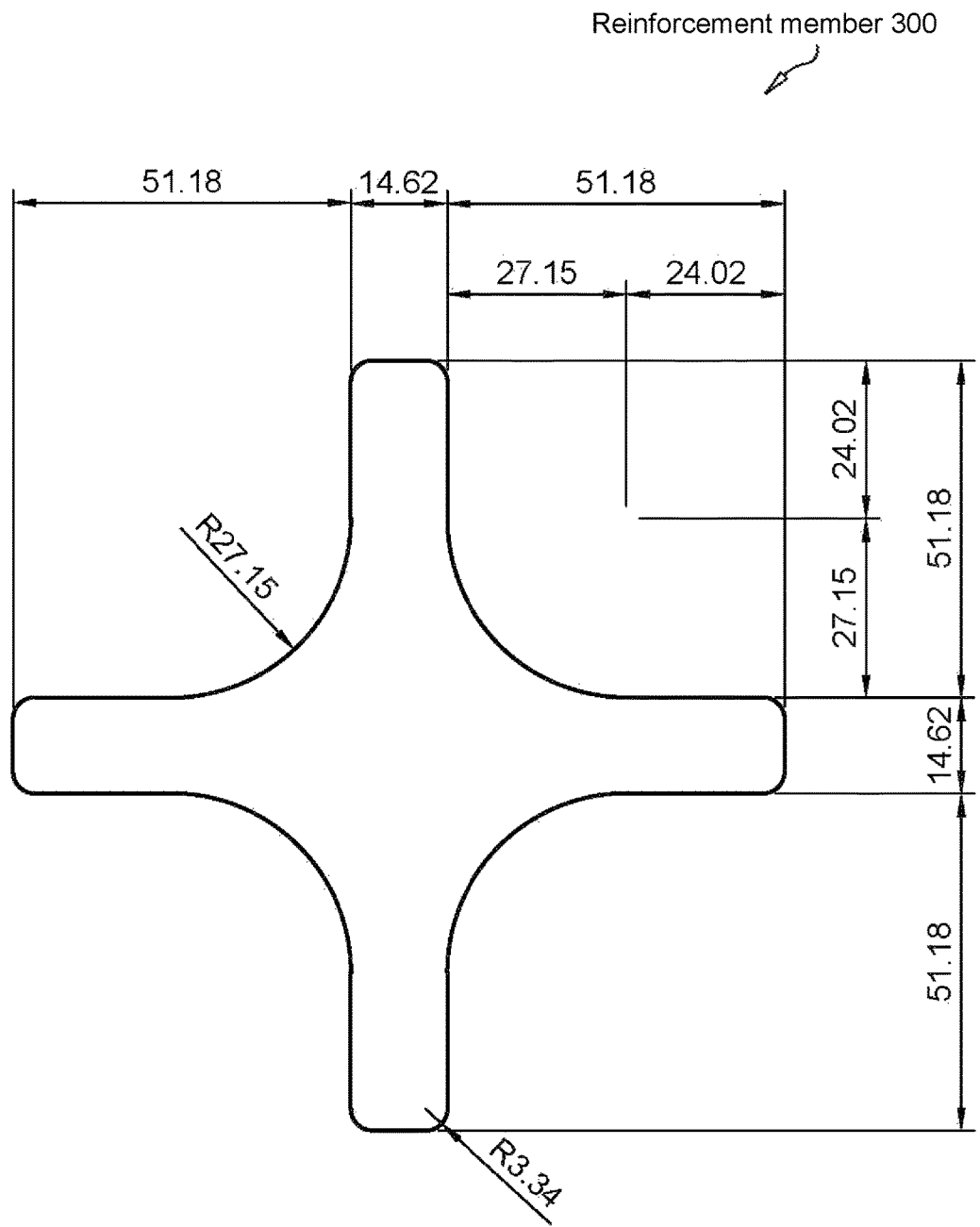
FIG. 3 is a top view of a reinforcement portion, in accordance with the present invention.

Looking now at FIG. 3, at least one reinforcement member 300, discussed above, integrates into the body portion 102. In one embodiment, the reinforcement member 300 has a generally X shape and is substantially less resilient than the body portion 102, so as to inhibit undesirable flexing of the joint 200. For example, when positioned centrally on the body portion 102, the X shape of the reinforcement member 300 helps inhibit forward and rearward flexing by an ankle or wrist.

In one embodiment, the reinforcement member has a length of about 117 centimeters and a radius curve of about 27.15° between the arms of the X shape. Though, the size and dimensions of the reinforcement member 300 may be altered to suit variously sized body portions 102. Though in other embodiments, the reinforcement member 300 can follow any variety of shapes and dimensions. In any case, the reinforcement member 300 is significantly more rigid than the body portion to provide additional stability.

Figure 4:
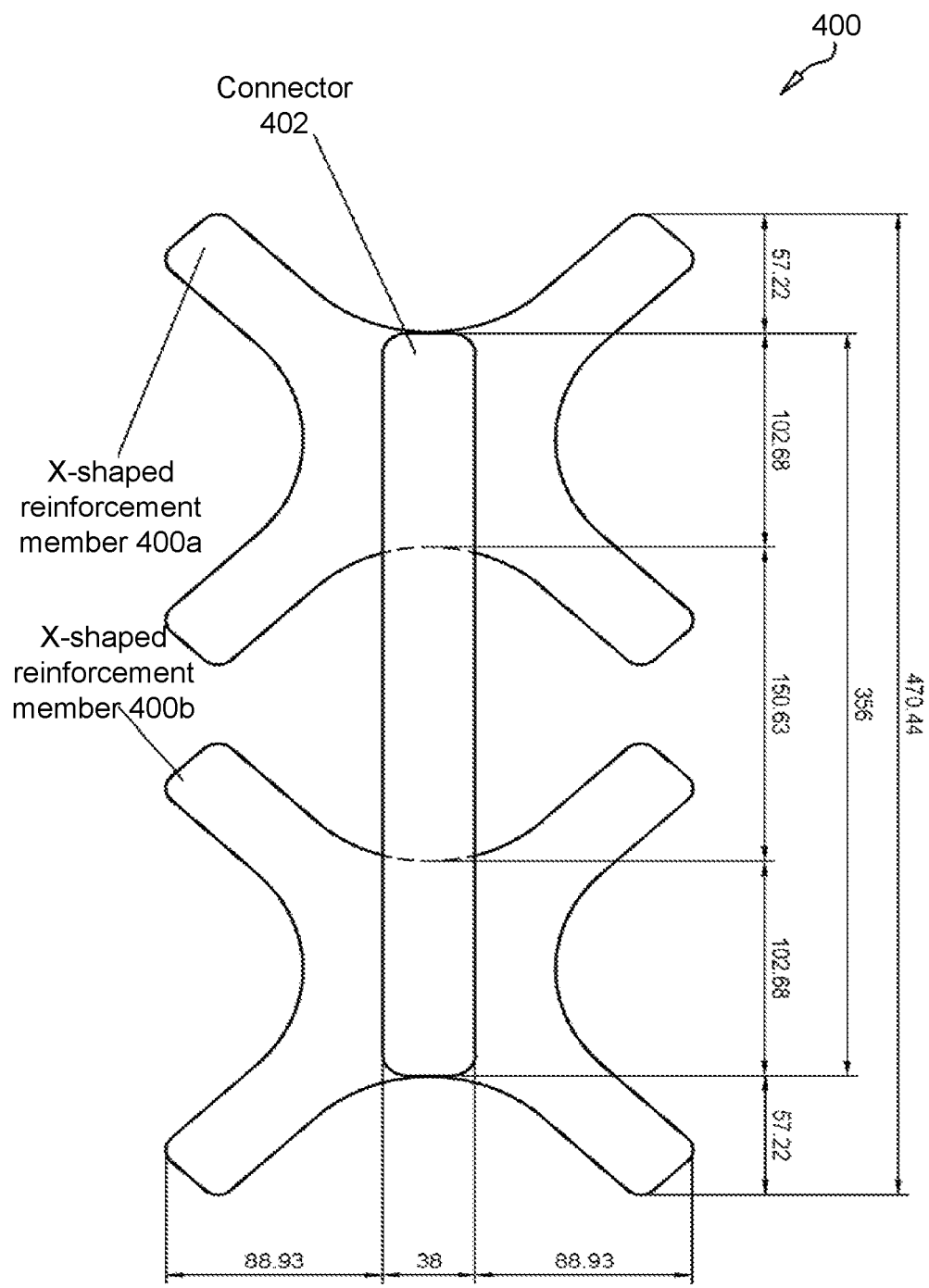
FIG. 4 is a top view of a pair of X-shaped reinforcement members, in accordance with the present invention.

In another embodiment illustrated in FIG. 4, a pair of ribbons 400a, 400b having a generally X shape is integrated into the body portion 102. The ribbons 400a, 400b provide the additional rigidity for stabilization of the joint 200, similar to the resilient member 300 discussed above. The pair of ribbons 400a, 400b may be stitched along the length of the body portion 102. In some embodiments, a connector 402 creates a junction between the pair of ribbons 400a, 400b for yet even greater rigidity. In this embodiment, the body portion 102 may be rotated around the joint 200 to align the ribbons 400a, 400b and the connector 402 with a desired region of the joint 200.

Figure 9:
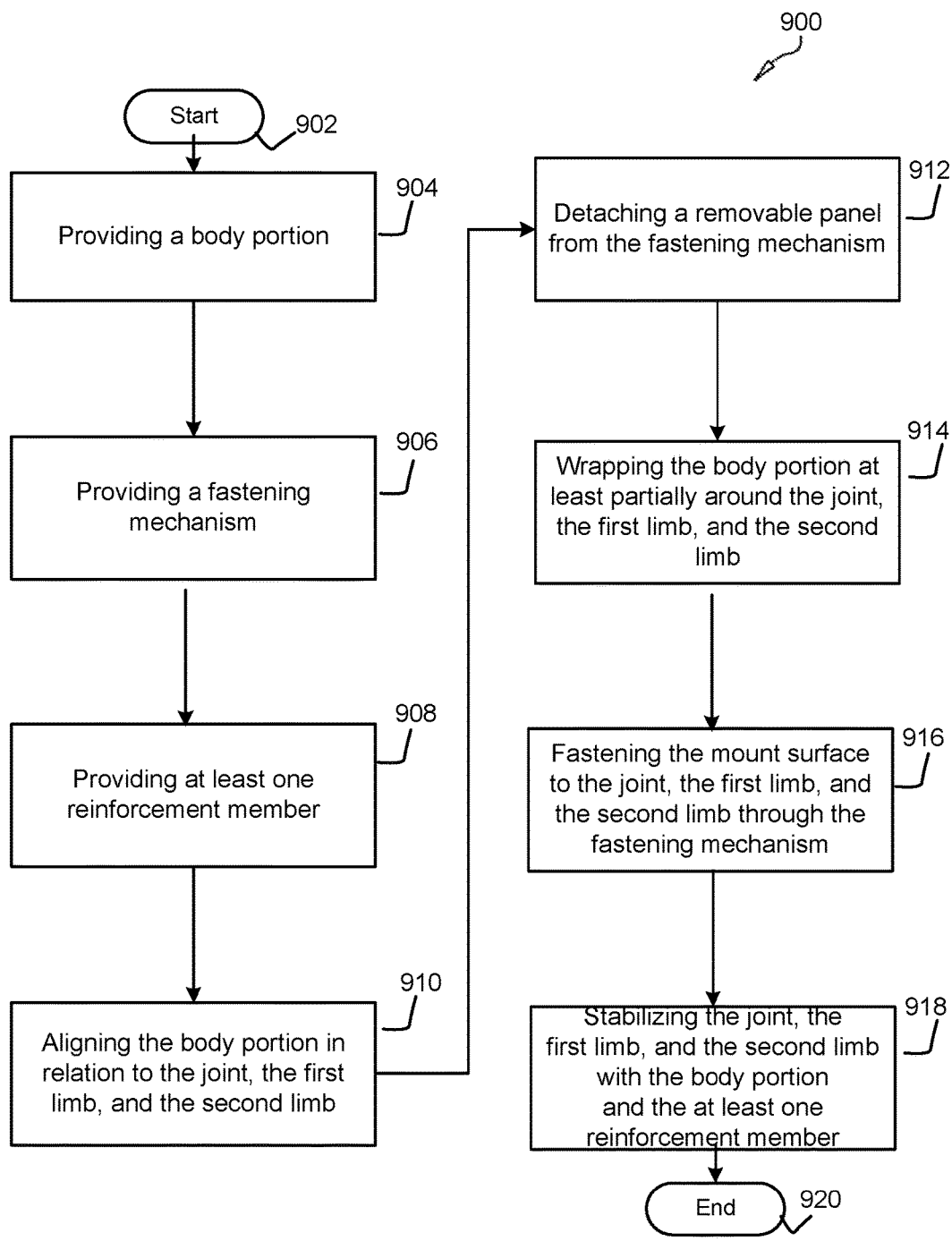
FIG. 9 illustrates a flowchart of an exemplary method for providing lateral and medial support to a joint with a reinforced joint support strap, in accordance with the present invention.

FIG. 9 illustrates a flowchart of an exemplary method 900 for providing lateral and medial support to a joint 200 with a support strap 100. The method 900 includes a starting Step 902 for initiating the means for joint 200 and limb 202, 204 stabilization. In some embodiments, the method 900 may include a Step 904 of providing a body portion 102, the body portion 102 defined by a generally elongated V-shape, the body portion 102 further defined by a pair of termini 104a, 104b, a base end 107, an open end 106, an exterior surface 120, and a mount surface 108, the body portion 102 being generally resilient. The body portion 102 forms a substantial portion of the support strap 100 that encapsulates the joint 200. The body portion 102 may be manipulated through rotation or axial movement along the limbs 202, 204 for an enhanced fit.

A Step 906 may include providing a fastening mechanism on the mount surface 108, the fastening mechanism configured to mount the body portion 102 on a joint 200, a first limb 202, and a second limb 204. The fastening mechanism may include, without limitation, a hook and loop fastener, an adhesive, a hook, a magnet, a button, and a buckle.

In some embodiments, a Step 908 includes providing at least one reinforcement member 116a, 116b, the at least one reinforcement member 116a, 116b defined by a lesser resilience (more rigidity) than the body portion 102. The at least one reinforcement member is configured to integrate into the body portion 102. The reinforcement member 116a, 116b is generally less resilient than the body portion 102. Because of the less resilient nature of the reinforcement member 116a, 116b, extra support to the joint 200 is consequently provided.

Figure 5:
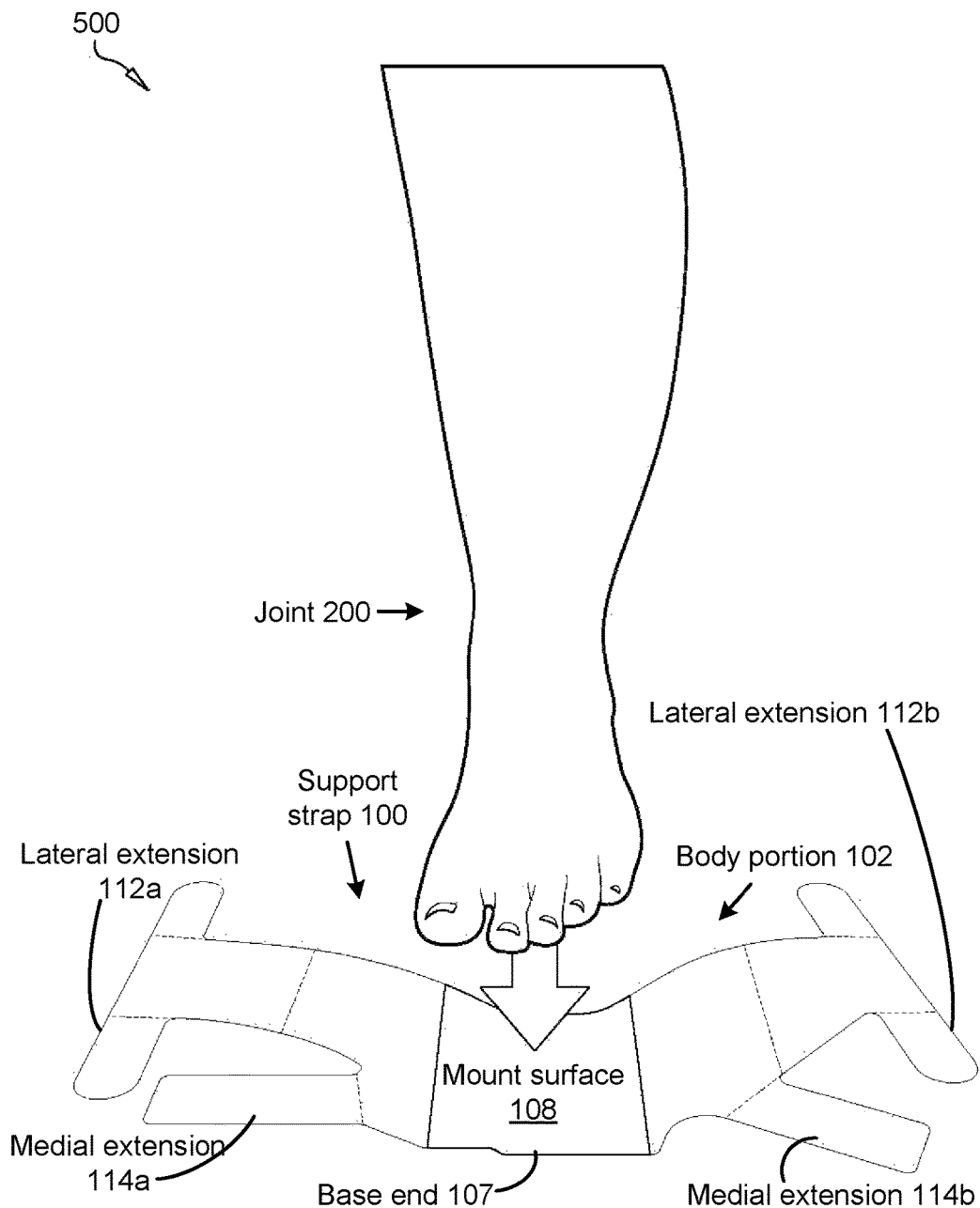
FIG. 5 is an environmental front perspective view of a joint, a first limb, and a second limb aligning with the reinforced joint support strap of FIG. 1, in accordance with the present invention.

A Step 910 may include aligning the body portion 102 in relation to the joint 200, the first limb 202, and the second limb 204, such that the mount surface 108 of the body portion 102 is exposed to engage the joint 200, the first limb 202, and the second limb 204. FIG. 5 illustrates a foot aligning directly over the body portion 102. Though the body portion 102 may also encapsulate a wrist, a knee, or a neck.

Figure 6:
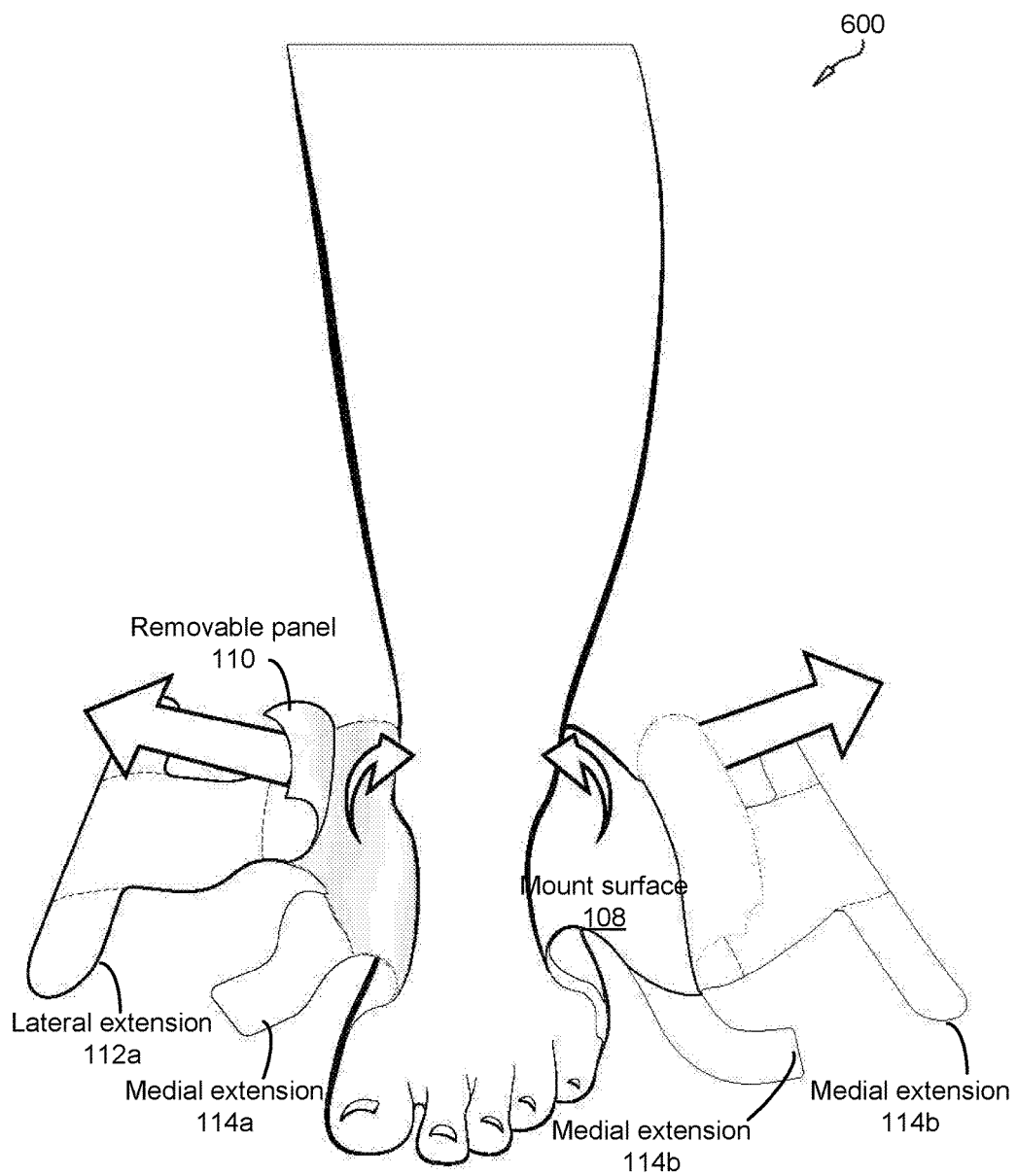
FIG. 6 is an environmental front perspective view of a removable panel from the reinforced joint support strap of FIG. 1 detaching from a mount surface to expose a fastening mechanism, in accordance with the present invention.

A further Step 912 includes detaching a removable panel 110 from the fastening mechanism. FIG. 6 illustrates the removable panel 110 peeling off the mount surface 108 to expose the fastening mechanism. The removable panel 110 enables selective operation of the fastening mechanism.

Figure 7:
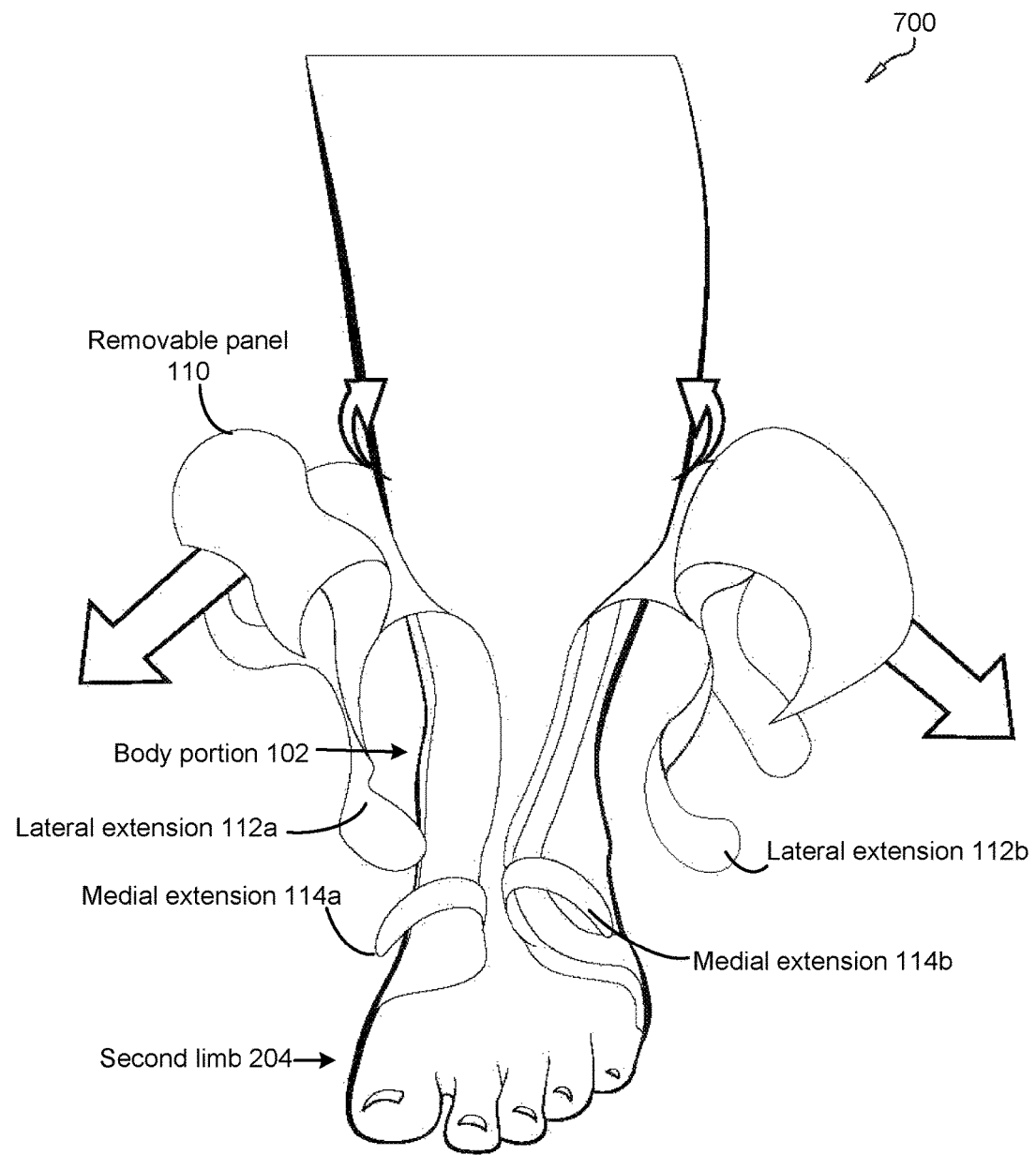
FIG. 7 is an environmental front perspective view of a joint, a first limb, and a second limb at least partially wrapping around the reinforced joint support strap in accordance with the present invention.

A Step 914 comprises wrapping the body portion 102 at least partially around the joint 200, the first limb 202, and the second limb 204. FIG. 7 shows the body portion 102, the at least one lateral extension 112a, 112b, and the at least one medial extension 114a, 114b encapsulating at least a portion of the joint 200, the first limb 202, and the second limb 204. As FIGS. 2 and 8 illustrate, the extensions 112a, 112b, 114a, 114b may be stretched in multiple directions around the limbs 202, 204, and fastened thereto to achieve a desired fit for the body portion 102.

A Step 916 may include fastening the mount surface 108 to the joint 200, the first limb 202, and the second limb 204 through the fastening mechanism. In one embodiment, one terminus 104a of the body portion 102 is folded back upon itself after wrapping around the joint 200, so as to join the fastening mechanism to the exterior surface 120 of the body portion 102. In another embodiment, the fastening mechanism fastens directly on the joint 200.

A Step 918 comprises stabilizing the joint 200, the first limb 202, and the second limb 204 with the body portion 102 and the at least one reinforcement member. FIG. 8 illustrates a right side perspective view of the support strap 100 fully encapsulating the joint 200, the first limb 202, and the second limb 204. An end Step 920 terminates the method 900. Though in one alternative embodiment, a second support strap may encapsulate the support strap 100 discussed here, so as to provide greater stability.

Figure 10A:
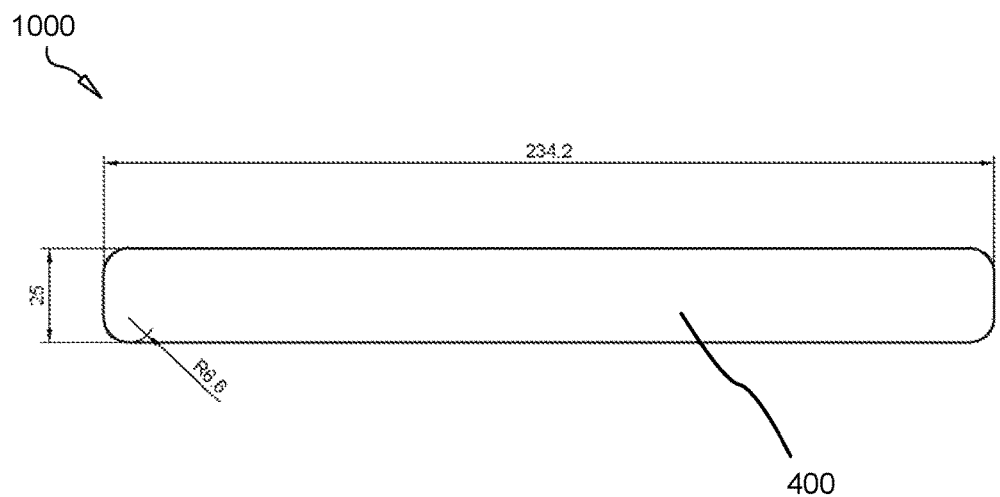
FIG. 10A illustrates a top perspective view of a reinforcement portion/ribbon in accordance with the present invention.
Figure 10B:
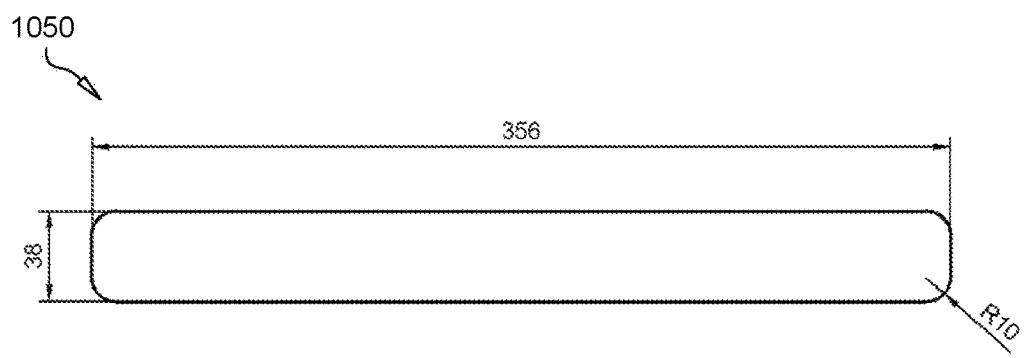
FIG. 10B illustrates a top perspective view of a reinforcement portion/ribbon in accordance with the present invention.

FIGS. 10A and 10B illustrate a top perspective view of a reinforcement portion/ribbon 1000 in accordance with the present invention. The reinforcement portion 400 (also known as a "ribbon") in the shown embodiment comprises a rectangular portion.

Figure 11A:
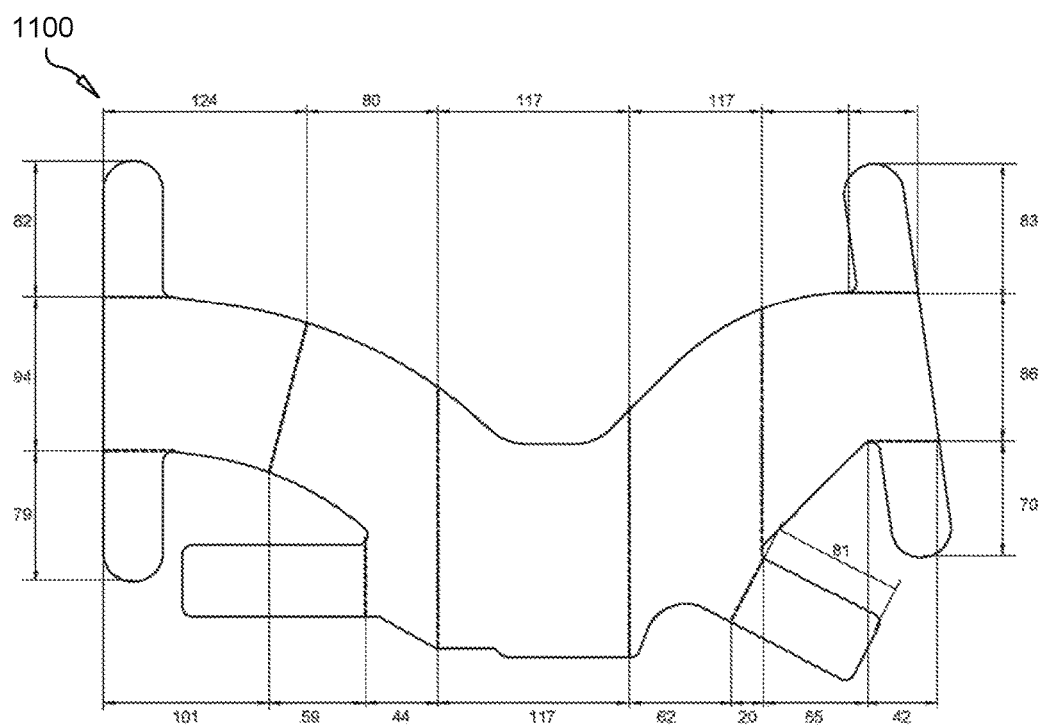
FIG. 11A illustrates a top perspective view of a joint support strap in accordance with the present invention.
Figure 11B:
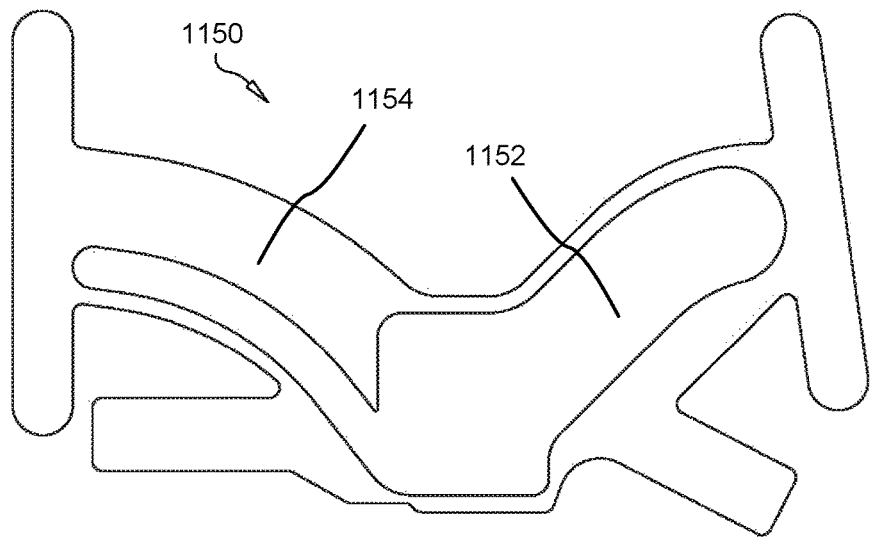
FIG. 11B illustrates a top perspective view of a reinforced joint support strap in accordance with the present invention.

FIG. 11A illustrates a top perspective view of a joint support strap 1100 in accordance with the present invention. FIG. 11B illustrates a top perspective view of a reinforced joint support strap 1150 in accordance with the present invention. The reinforced joint strap 1150 comprises an irregularly-shaped ribbon 1152 which a jutting lateral component 1154 comprising a curved rectangular protrusion from the main body of the ribbon 400.

Figure 12:
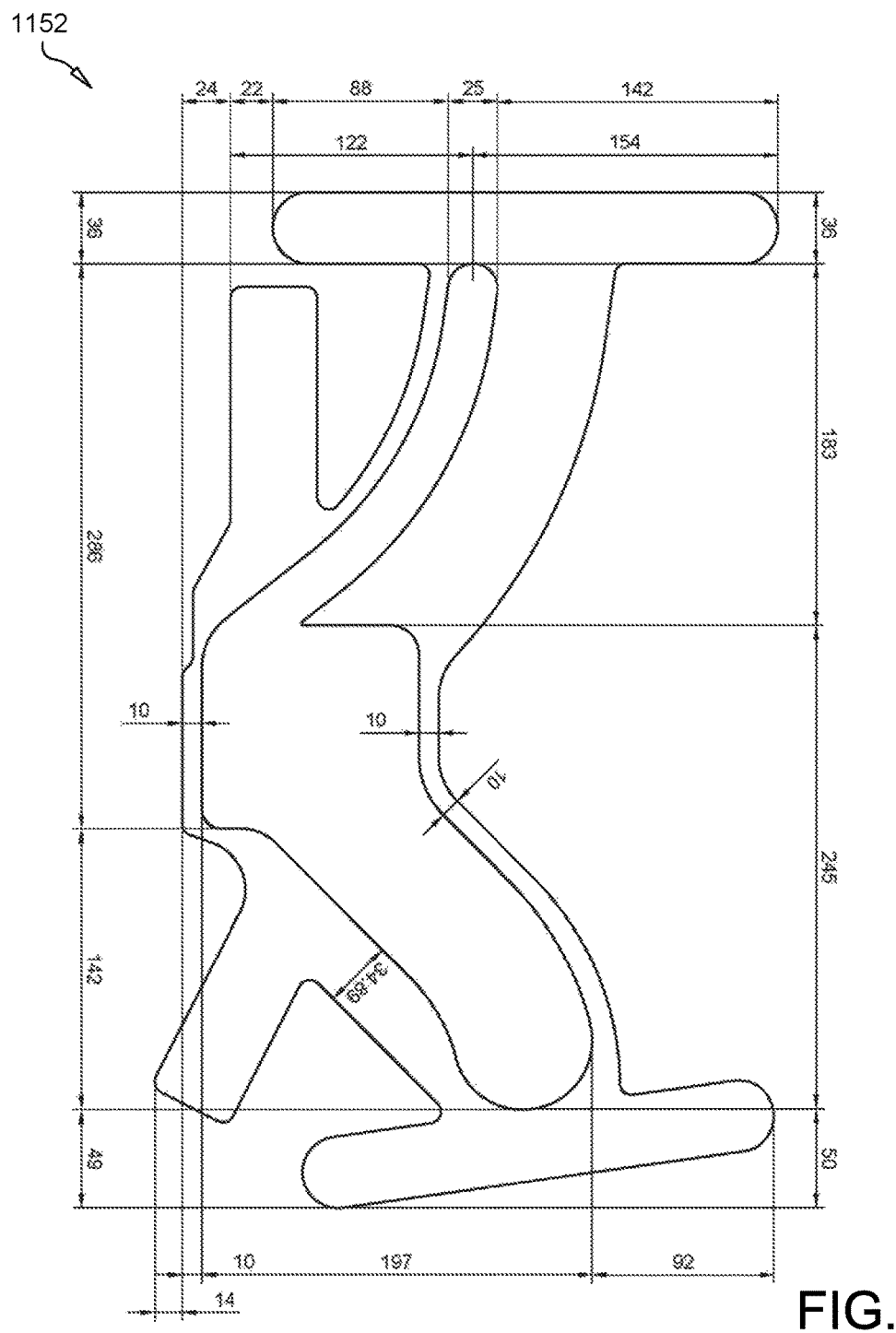
FIG. 12 illustrates a top perspective view of a reinforced joint support strap in accordance with the present invention.
Figure 13:
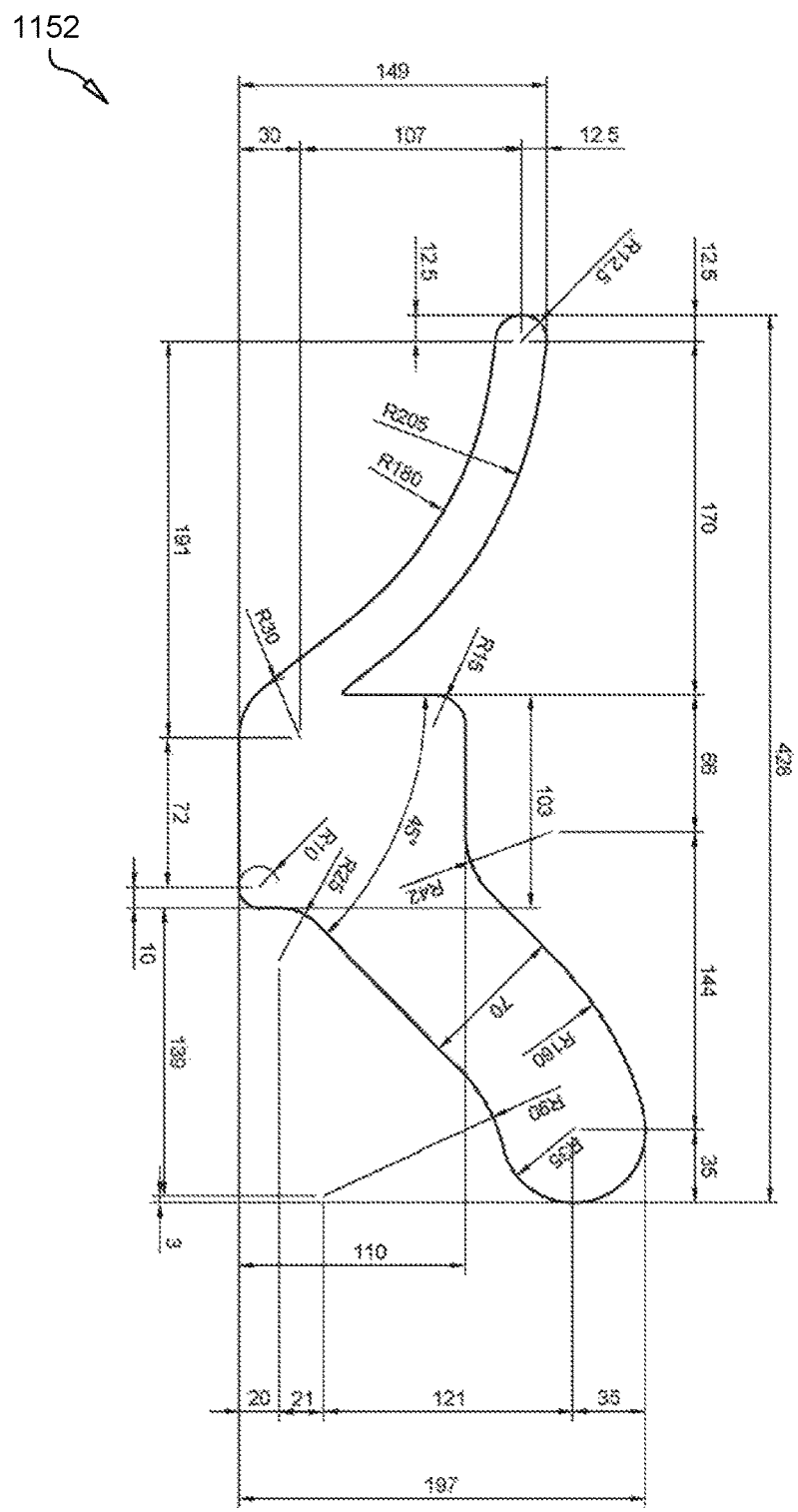
FIG. 13 illustrates a top perspective view of a reinforced joint support strap in accordance with the present invention.

FIGS. 12 and 13 illustrate a top perspective view of a ribbon 1152 in accordance with the present invention.

Dimensions are shown in these figures, which apply in some embodiments. Other embodiments may include ribbons 400, 1152 with larger or smaller dimensions which may be otherwise shaped.

Figure 14:
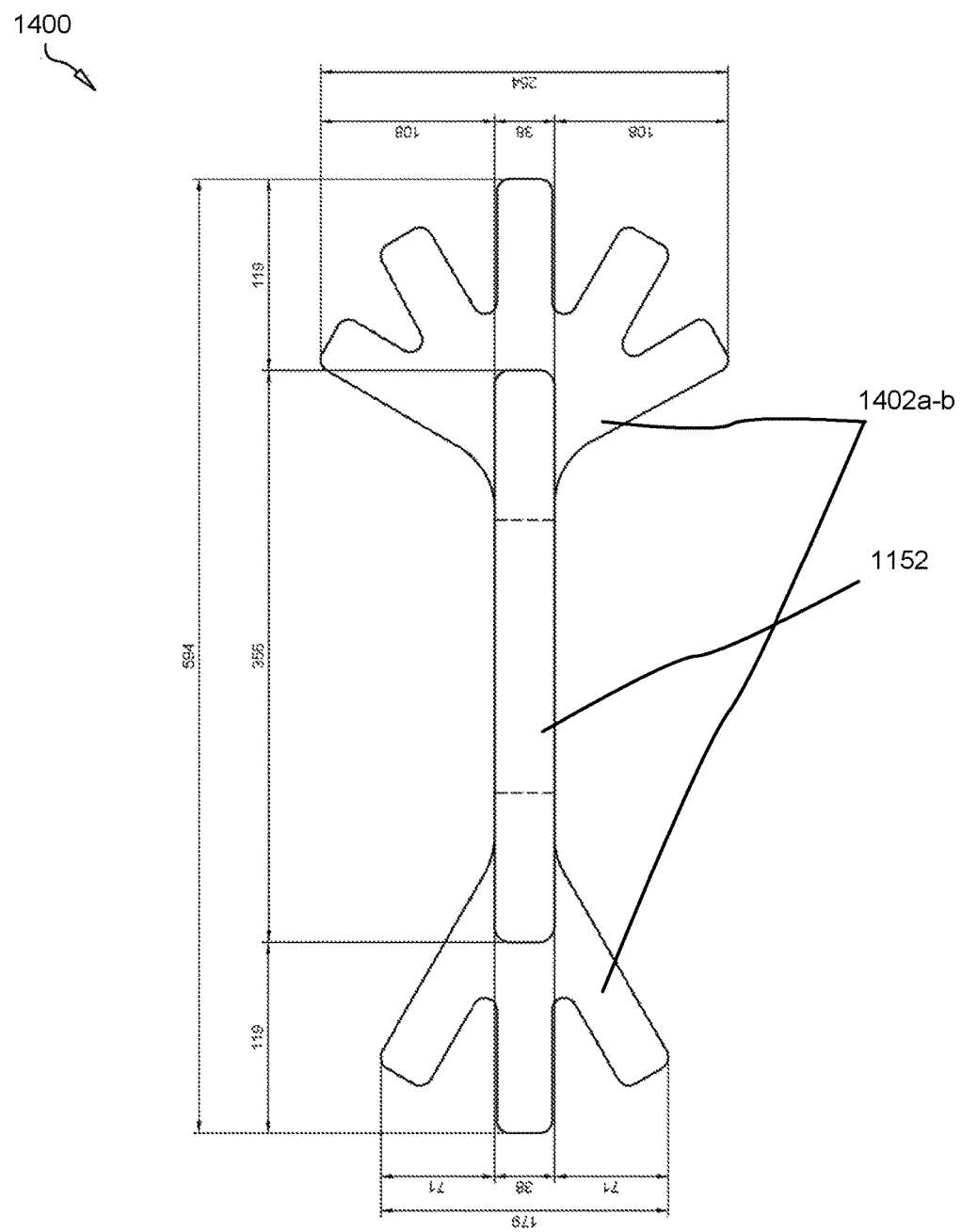
FIG. 14 illustrates a top perspective view of a reinforcement portion in accordance with the present invention.

FIG. 14 illustrates a top perspective view of a reinforcement portion 1400 in accordance with the present invention. As shown, the reinforcement portion in the shown embodiment comprises a rectangular ribbon affixed to and interconnecting two Y-Shaped ribbons 1402 having a plurality of fingers. In various embodiments, the Y-Shaped ribbons have between two and eight or more fingers.

Figure 15:
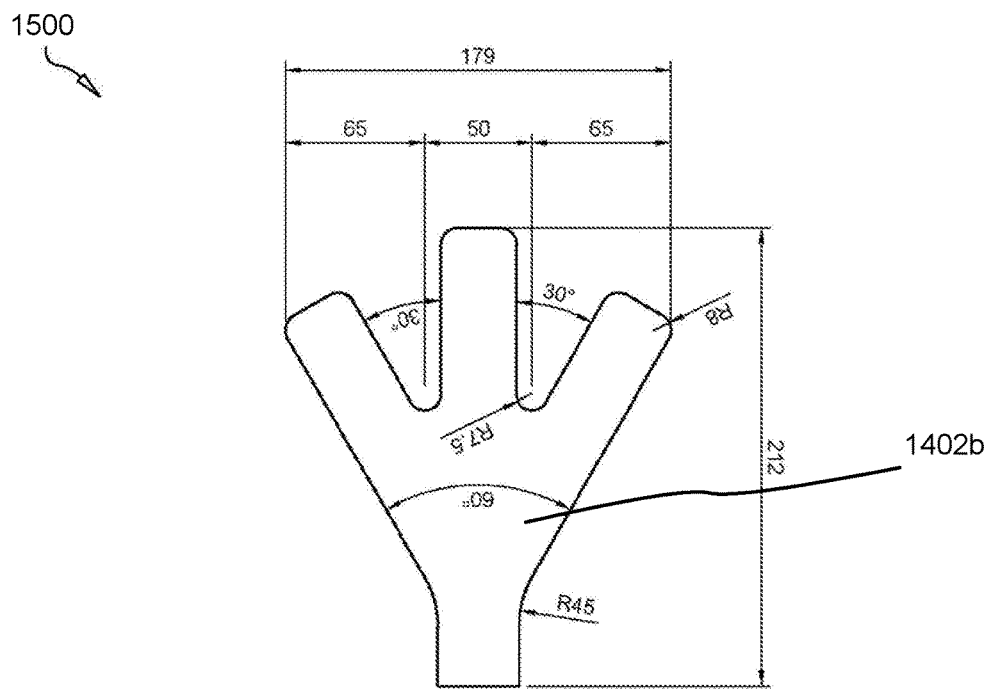
FIG. 15 illustrates a top perspective view of a reinforcement portion in accordance with the present invention.
Figure 15:
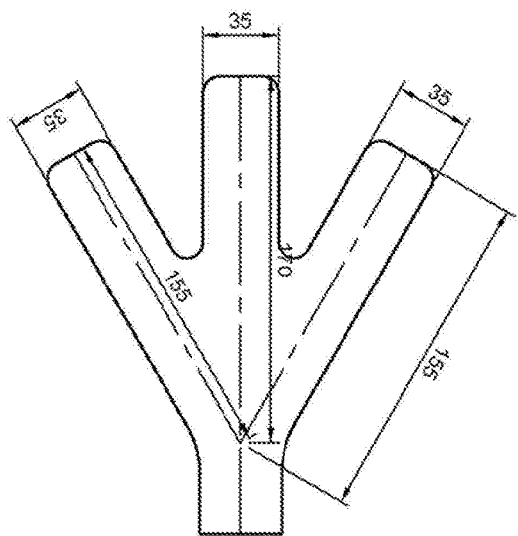
Figure 16:
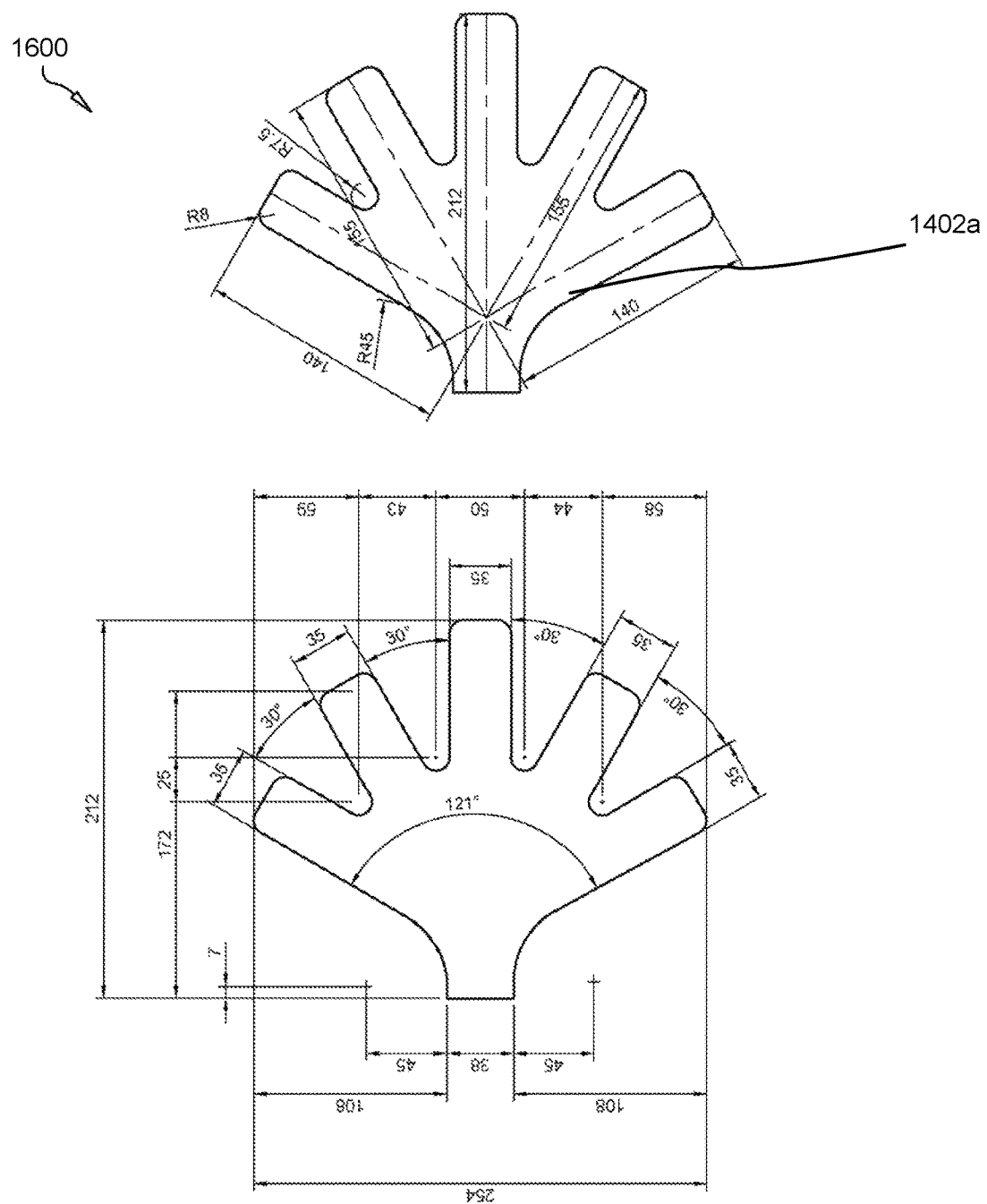
FIG. 16 illustrates a top perspective view of a reinforcement portion in accordance with the present invention.

FIG. 15 illustrates a top perspective view of a the Y-Shaped member of a reinforcement portion in accordance with the present invention. FIG. 16 illustrates a top perspective view of a Y-Shaped reinforcement portion in accordance with the present invention. The shown ribbon 1600 comprises five fingers as shown.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A support strap for providing lateral and medial support to a joint, the strap comprising:
    a body portion defined by a generally elongated V-shape defined by a pair of termini, a base end, an open end, an exterior surface, and a mount surface, the body portion comprising an elasticized member configured to enable resilience;
    a fastening mechanism enabling detachable mounting of the strap;
    a removable panel detachably overlaying the fastening mechanism to enable selective operation of the fastening mechanism;
    at least one lateral extension extending from at least one of the pair of termini of the body portion;
    at least one medial extension extending from the base end of the body portion,
    whereby the body portion, the at least one lateral extension, and the at least one medial extension are configured to cooperate to immobilize the joint against lateral and medial mobility, while providing resistance to twisting of a first limb relative to a second limb; and
    at least one reinforcement member, the at least one reinforcement member defined by a lesser resilience than the body portion, the at least one reinforcement member being integrated into the body portion,
    whereby the at least one reinforcement member is further configured to enhance immobilization of the joint against lateral and medial mobility.

2. The strap of claim 1, wherein the body portion is configured to enable wrapping around the joint while extending along lateral and medial sides of the first limb adjacent the joint.

3. The strap of claim 1, wherein the joint comprises an ankle or a wrist.

4. The strap of claim 1, wherein the body portion is configured to enable wrapping around a muscle.

5. The strap of claim 1, wherein the elasticized member includes at least one member selected from the group consisting of: elastic, rubber, nylon, polyester, and a resilient polymer.

6. The strap of claim 1, wherein the body portion comprises an anti-bacterial composition.

7. The strap of claim 1, wherein the at least one lateral extension is disposed approximately at the pair of termini of the body portion.

8. The strap of claim 1, wherein the at least one lateral extension comprise a pair of spaced-apart parallel lateral extensions.

9. The strap of claim 1, wherein the at least one medial extension is disposed approximately at the base end of the body portion.

10. The strap of claim 1, wherein the fastening mechanism is disposed on the mount surface.

11. The strap of claim 10, wherein the exterior surface comprises a corresponding fastening mechanism for joining with the fastening mechanism on the mount surface.

12. The strap of claim 1, wherein the removable panel is configured to peel off the mount surface.

13. The strap of claim 1, wherein the fastening mechanism includes at least one member selected from the group consisting of: a hook and loop fastener, an adhesive, a hook, a magnet, a button, and a buckle.

14. The strap of claim 1, wherein the exterior surface of the body portion is configured to at least partially restrict passage of moisture and contaminants.

15. The strap of claim 1, wherein the at least one reinforcement member comprises a pair of Y-shaped reinforcement members having substantially less resilience than the body portion, the Y-shaped reinforcement members having between two and eight fingers.

16. The strap of claim 1, wherein the at least one reinforcement member comprises a length of about 117 centimeters.

17. The strap of claim 1, wherein the at least one reinforcement member comprises a radius curve of about 27.15 degrees.

18. The strap of claim 1, further including a connector, the connector configured to join the at least one reinforcement member.

* * * * *